(12) United States Patent
Lu et al.

(10) Patent No.: US 10,888,372 B2
(45) Date of Patent: Jan. 12, 2021

(54) RADIOFREQUENCY ABLATION ELECTRODE NEEDLE

(71) Applicants: Industrial Technology Research Institute, Hsinchu (TW); National Taiwan University Hospital, Taipei (TW)

(72) Inventors: Hui-Hsin Lu, New Taipei (TW); Meng-Han Tsai, Zhubei (TW); Kai-Wen Huang, Taipei (TW); Jo-Ping Lee, Tainan (TW); Wen-Yang Chou, Zhubei (TW)

(73) Assignees: INDUSTRIAL TECHNOLOGY RESEARCH INSTITUTE, Hsinchu (TW); NATIONAL TAIWAN UNIVERSITY HOSPITAL, Taipei (TW)

( * ) Notice: Subject to any disclaimer, the term of this patent is extended or adjusted under 35 U.S.C. 154(b) by 957 days.

(21) Appl. No.: 15/378,852

(22) Filed: Dec. 14, 2016

(65) Prior Publication Data

US 2017/0215946 A1 Aug. 3, 2017

Related U.S. Application Data

(60) Provisional application No. 62/339,955, filed on May 23, 2016, provisional application No. 62/288,422, filed on Jan. 28, 2016.

(51) Int. Cl.
*A61B 18/14* (2006.01)
*A61B 18/00* (2006.01)
(52) U.S. Cl.
CPC .......... *A61B 18/1477* (2013.01); *A61B 18/14* (2013.01); *A61B 2018/00083* (2013.01);
(Continued)

(58) Field of Classification Search
CPC ................ A61B 18/14; A61B 18/1477; A61B 2018/00083; A61B 2018/00107;
(Continued)

(56) References Cited

U.S. PATENT DOCUMENTS 5,807,395 A 9/1998 Mulier et al.
5,893,885 A 4/1999 Webster, Jr.
(Continued)

FOREIGN PATENT DOCUMENTS

CN 200954136 Y 10/2007
CN 102883674 A 1/2013
(Continued)

OTHER PUBLICATIONS

Chu et al., "Thermal ablation of tumours: biological mechanisms and advances in therapy." Nature Reviews Cancer, Mar. 2014, vol. 14, No. 3, 199-208.
(Continued)

*Primary Examiner* — Michael F Peffley
*Assistant Examiner* — Amanda L Zink
(74) *Attorney, Agent, or Firm* — Birch, Stewart, Kolasch & Birch, LLP (57) ABSTRACT

A radiofrequency ablation electrode needle includes at least one first segment and at least two second segments. The at least one first segment and the at least two second segments are exposed on a surface of the needle body. An impedance of the at least one first segment is smaller than an impedance of the at least two second segments and at least one of the at least one first segment is disposed between two immediately adjacent ones of the at least two second segments. Besides, the radiofrequency ablation electrode needle is a monopolar electrode needle.

19 Claims, 8 Drawing Sheets

(52) U.S. Cl.
CPC ............... *A61B 2018/00107* (2013.01); *A61B 2018/00577* (2013.01); *A61B 2018/00601* (2013.01); *A61B 2018/1475* (2013.01)

(58) Field of Classification Search
CPC ........... A61B 2018/00577; A61B 2018/00601; A61B 2018/1475
See application file for complete search history.

(56) References Cited

U.S. PATENT DOCUMENTS

| | | | | |
|---|---|---|---|---|
| 6,092,528 | A * | 7/2000 | Edwards | A61N 1/056 128/898 |
| 7,115,124 | B1 * | 10/2006 | Xiao | A61B 18/1477 606/41 |
| 8,738,125 | B1 * | 5/2014 | Heller | A61N 1/327 604/21 |
| 9,283,031 | B2 | 3/2016 | Janssen et al. | |
| 2001/0020166 | A1 | 9/2001 | Daly et al. | |
| 2009/0299417 | A1 * | 12/2009 | Schoenbach | A61N 1/327 607/2 |
| 2010/0049178 | A1 * | 2/2010 | Deem | A61B 18/02 606/9 |
| 2013/0158442 | A1 * | 6/2013 | Demarais | A61F 7/12 601/3 |
| 2014/0039481 | A1 | 2/2014 | Coe et al. | |
| 2014/0058374 | A1 | 2/2014 | Edmunds et al. | |

FOREIGN PATENT DOCUMENTS

| | | |
|---|---|---|
| CN | 102908191 A | 2/2013 |
| CN | 202982207 U | 6/2013 |
| CN | 104688333 A | 6/2015 |
| CN | 104720890 A | 6/2015 |
| EP | 1 059 067 A1 | 12/2000 |
| TW | M466637 U | 12/2000 |
| WO | WO 2010/137920 A2 | 12/2010 |
| WO | WO 2011/113943 A1 | 9/2011 |
| WO | WO 2015/080411 A1 | 6/2015 |

OTHER PUBLICATIONS

Chua et al., "Pulsed radiofrequency treatment in interventional pain management: mechanisms and potential indications—a review", Acta Neurochir, 2011, vol. 153, No. 4, 763-771.

Kelogrigoris et al., "Percutaneous radiofrequency ablation for malignant liver tumours in challenging locations", Journal of Medical Imaging and Radiation Oncology, 2012, vol. 56, No. 1. 48-54.

Miao et al., "Ex Vivo Experiment on Radiofrequency Liver Ablation with Saline Infusion through a Screw-Tip Cannulated Electrode", Journal of Surgical Research, Jul. 15, 1997, vol. 71, No. 1, 19-24, Article No. JR975133.

Mulier et al. "Electrodes and multiple electrode systems for radiofrequency ablation: a proposal for updated terminology." European radiology, 2005, vol. 15, No. 4, 798-808.

Mulier et al., "Size and geometry of hepatic radiofrequency lesions" European Journal of Surgical Oncology (EJSO), 2003, vol. 29, No. 10, 867-878.

Ni et al. "A review of the general aspects of radiofrequency ablation." Abdominal imaging, Mar. 23, 2005, vol. 30, No. 4, 381-400.

Park et al. "Comparison of therapeutic efficacy and safety of radiofrequency ablation of hepatocellular carcinomas between internally cooled 15-G and 17-G single electrodes." The British journal of radiology, 2014, vol. 87, No. 1036, 20130534.

Rhim et al., "Essential Techniques for Successful Radio-frequency Thermal Ablation of Malignant Hepatic Tumors 1", RadioGraphics, Oct. 2001, vol. 21, suppl_1, S17-S39.

Solazzo et al. "Radiofrequency Ablation: Importance of Background Tissue Electrical Conductivity—An Agar Phantom and Computer Modeling Study 1." Radiology, 2005, vol. 236, No. 2, 495-502.

Solazzo et al., "High-Power Generator for Radiofrequency Ablation: Larger Electrodes and Pulsing Algorithms in Bovine ex Vivo and Porcine in Vivo Settings", Radiology, Mar. 2007, vol. 242, No. 3, 743-750.

Taiwanese Office Action and Search Report, dated Sep. 11, 2017, for Taiwanese Application No. 105141401.

* cited by examiner

RADIOFREQUENCY ABLATION ELECTRODE NEEDLE

CROSS-REFERENCE TO RELATED APPLICATION

This application claims the priority benefits of U.S. Provisional Application No. 62/288,422, filed on Jan. 28, 2016 and U.S. Provisional Application No. 62/339,955, filed on May 23, 2016. The entirety of each of the above-mentioned patent applications is hereby incorporated by reference herein and made a part of this specification.

TECHNICAL FIELD

The technical field relates to a radiofrequency ablation electrode needle, and more particularly, relates to a monopolar radiofrequency ablation electrode needle.

BACKGROUND

A radiofrequency ablation (RFA) therapy is a widely used tumor ablation technique. When performing the RFA therapy, the doctor inserts an electrode needle accurately into the tumor area under a guidance imaging such as ultrasound, computed tomography (CT), magnetic resonance imaging (MRI). The electrode needle will release radio frequency waves, and the tissue which the radio frequency waves pass through will generate thermal energy due to ion agitation, so that the temperature of the treatment area starts to rise. When the temperature of the treatment area reaches over 45 Celsius degree, it will result in coagulation necrosis of the tissue with the tumor in the treatment area.

However, during the RFA therapy, the necrosis of the tissue will cause the impedance (as well as the temperature) of the tissue to rise, and the radiofrequency ablation system has to temporally stop operating from time to time in order to reduce the temperature of the heated tissue, which makes the RFA therapy inefficient and longer. In addition, the most liver tumors that are less than three center meters in diameter are sphere-like, and thus an ellipsoid-like ablation shape will make more normal tissue around the tumor necrosis caused from the existing single needle electrodes or from the non-expansion-type electrodes.

SUMMARY

According to an embodiment of the disclosure, a radiofrequency ablation electrode needle includes a needle body comprising at least one first segment and at least two second segments, wherein the at least one first segment and the at least two second segments are exposed on a surface of the needle body, wherein an impedance of the at least one first segment is smaller than an impedance of the at least two second segments, at least one of the at least one first segment is disposed between two immediately adjacent ones of the at least two second segments, and the radiofrequency ablation electrode needle is a monopolar electrode needle.

The foregoing will become better understood from a careful reading of a detailed description provided herein below with appropriate reference to the accompanying drawings.

DETAILED DESCRIPTION OF DISCLOSED EMBODIMENTS

Below, exemplary embodiments will be described in detail with reference to accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

The disclosure relates to a radiofrequency ablation electrode needle, which may ablate tissue faster to decrease total operation time.

The disclosure also relates to a radiofrequency ablation electrode needle that can achieve an ablation shape similar to a sphere to meet clinical needs.

Figure 1:
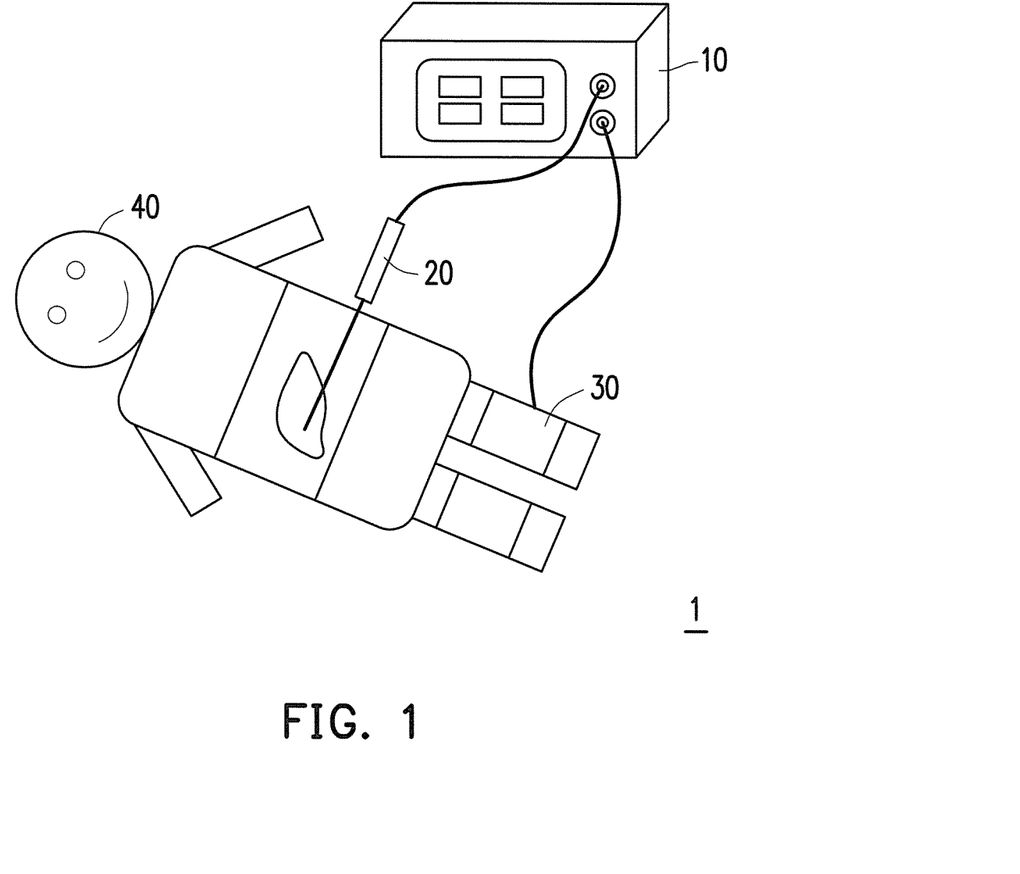
FIG. 1 is a schematic diagram of a radiofrequency ablation system according to an exemplary embodiment of the disclosure.

FIG. 1 is a schematic diagram of a radiofrequency ablation system according to an exemplary embodiment of the disclosure. The radiofrequency ablation system 1 comprises a radiofrequency generator 10, a radiofrequency ablation electrode needle 20, and a pair of return pads 30. In the radiofrequency ablation system 1, the radiofrequency generator 10 may generate a radiofrequency current with a frequency ranged from 300 to 500 kHz and a power ranged less than 1000 W. The radiofrequency ablation electrode needle 20 is a monopolar electrode needle and operated by directly inserting it in an affected area of a patient 40. The pair of the return pads 30 is affixed to the patient's thighs or dorsum. The radiofrequency ablation system 1 operates in an ohmic heating manner to forms a circuit loop between the radiofrequency ablation electrode needle 20 and the pair of the return pads 30, and generates a high current density in an area around the radiofrequency ablation electrode needle 20 to ablate a tumor or a treatment area.

In an impedance control mode, a current or a voltage is controlled by giving a constant voltage and measuring changes of the impedance of the circuit loop between the radiofrequency ablation electrode needle 20 and the return pads 30 during the radiofrequency ablation therapy. The current will cause ion friction in the tissue and produce heat to raise the local temperature. For a biological subject, the biological tissue necrosis will occur when the temperature is over 45 Celsius degree. While the impedance is too large, usually over an initial impedance threshold, the radiofrequency generator 10 will temporally stop operating to reduce the temperature of the heated tissue around the radiofrequency ablation electrode needle 20. After a while (for example, a predetermined time period), the radiofrequency generator 10 will restart and radiofrequency ablation system 1 proceeds to ablate. Therefore, the stopping time and times of the radiofrequency generator 10 may influence the whole therapy time and the ablation results.

Besides, in a general radiofrequency ablation system, the conductive part responsible for delivering the current is a direction along the radiofrequency ablation electrode needle, which cause the ablation shape similar to an ellipsoid with a major axis extending along two ends of the conductive part. Take hepatocellular carcinoma (HCC) for example, HCC is the most common form of cancer that is treated with the radiofrequency ablation therapy. The liver tumor under 3 cm usually has a sphere-like shape, and the resection tumor margin is suggested to the at least 0.5 to 1 cm. Therefore, the known radiofrequency ablation electrode needle will result in unnecessary ablation of the normal tissue when applied to a liver tumor with a sphere-like shape due to the ellipsoid-like ablation shape.

As a result, in one embodiment of the disclosure, a radiofrequency ablation electrode needle 20 may ablate the tissue faster to decrease total operation time.

In another embodiment of the disclosure, a radiofrequency ablation electrode needle 20 has a sphere-like ablation shape to meet clinical needs.

Figure 2A:
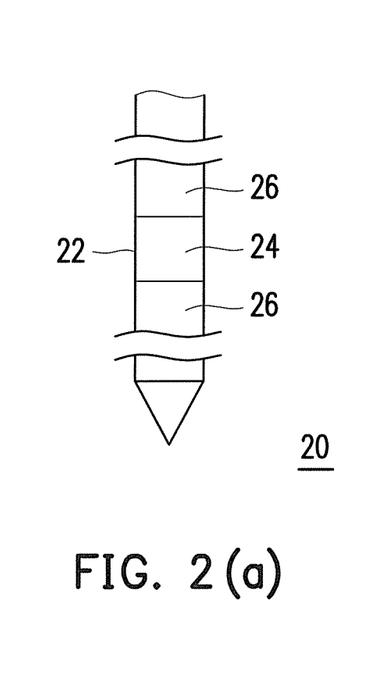
FIGS. 2(a)-2(b) are schematic diagrams of a radiofrequency ablation electrode needle according to exemplary embodiments of the disclosure.

For the different designs of the radiofrequency ablation electrode needle 20, the embodiments are presented below:

FIG. 2(a) is a schematic diagram of a radiofrequency ablation electrode needle according to an exemplary embodiment of the disclosure. The radiofrequency ablation electrode needle 20 comprises a needle body 22 comprising at least one first segment 24 and at least two second segments 26, wherein the at least one first segment 24 and the at least two second segments 26 are exposed on a surface of the needle body 22, wherein an impedance of the at least one first segment 24 is smaller than an impedance of the at least two second segments 26, at least one of the at least one first segment 24 is disposed between two immediately adjacent ones of the at least two second segments 26, and the radiofrequency ablation electrode needle 22 is a monopolar electrode needle.

In the embodiment, the difference between the impedance of the at least one first segment 24 and the impedance of the at least two second segments is at least $10^{65}\Omega$ In some embodiments, the material of the at least one first segment 24 may be, but not limited to, biocompatible metallic or alloy materials such as stainless steel, titanium, nickel and so on, or biocompatible conductive materials such as carbon, conductive polymer and so on, and the material of the at least two second segments 26 may be, but not limited to, ceramic or other biocompatible non-conductive polymers.

Figure 2B:
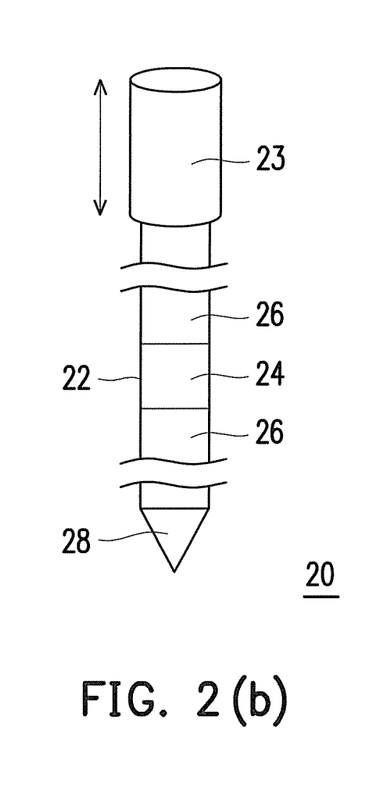

FIG. 2(b) is a schematic diagram of a radiofrequency ablation electrode needle according to another exemplary embodiment of the disclosure. General speaking, in order to treat/ablate multiple tumors with different sizes during a single operation, an existing practice is to replace radiofrequency ablation electrode needles different sizes respectively for the tumors with different sizes. In order to make the operation more efficient, in an embodiment as shown in FIG. 2(b), the radiofrequency ablation electrode needle 20 further comprises an insulating cover 23 disposed outside the needle body 22. The insulating cover 23 is extendable and retractable to selectively expose partial of the first segment 24 and partial of the second segments 26. More specifically, the area covered by the insulating cover 23 will not causes radiofrequency ablation, and only the area of the radiofrequency ablation electrode needle 20 that is not covered by the insulating cover 23 will cause radiofrequency ablation. This allows the physician to adjust the size of the radiofrequency ablation to ablate the tumors with different sizes during a single operation, without the need to replace the radiofrequency ablation electrode needles with different sizes. By the design of the insulating cover 23, the physician may slide the insulating cover 23 to adjust the exposed area of the first segment 24 and the second segments 26 according to the size of the individual tumor without the need to change the currently used radiofrequency ablation electrode needle. In the illustrated embodiment, the insulating cover 23 is fully around the circumference of the needle body 22. In another embodiment, the insulating cover 23 may be partially around the circumference of the needle body 22. For example, the insulating cover 23 may only cover a half of the circumference of the needle body 22 such that the ablation shape of the radiofrequency ablation electrode needle 20 will become half, compared to the ablation shape of the radiofrequency ablation electrode needle 20 without the insulating cover 23.

Besides, in the embodiment, the pinpoint 28 of the needle body 22 is electrically insulated, and thus may prevent or slow down the rate of necrosis of surrounding tissue.

Figure 3A:
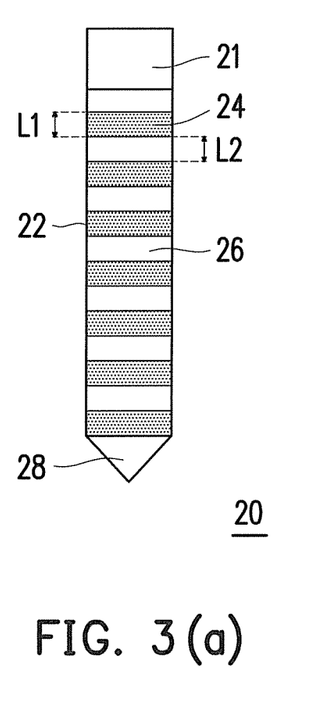
FIGS. 3(a)-3(e) are schematic diagrams of a radiofrequency ablation electrode needle according to exemplary embodiments of the disclosure.

FIG. 3(a) is a schematic diagram of a radiofrequency ablation electrode needle according to an exemplary embodiment of the disclosure. In the embodiment, the at least one first segment 24 includes a plurality of first segments 24, and the plurality of first segments 24 are electrically connected to each other, thereby making the radiofrequency ablation electrode needle 20 a monopolar electrode needle.

Besides, in an embodiment, the radiofrequency ablation electrode needle 20 further comprises an insulating part 21. An end of the insulating part 21 is connected to the needle body 22, and the other end of the insulating part 21 is connected to a handle for use by a physician.

Figure 3B:
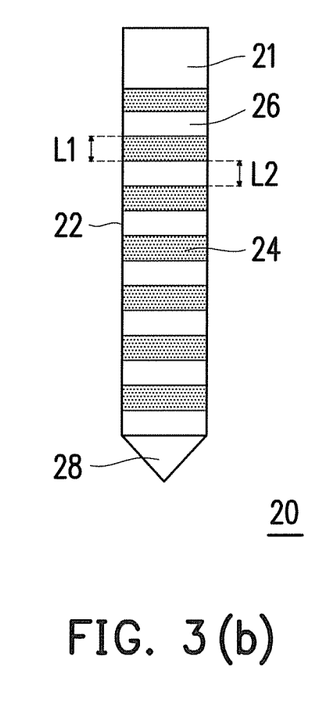

FIG. 3(b) is a schematic diagram of a radiofrequency ablation electrode needle according to another exemplary embodiment of the disclosure. In an embodiment, the first segments 24 and the second segments 26 are respectively exposed on the surface of the needle body 22 in a coated manner. In the embodiment of FIG. 3(a), the first segments 24 are a plurality of separate coatings coated on the surface of the needle body 22, and areas of the needle body 22 that are not covered by the plurality of separate coatings form the second segments 26. In the embodiment of FIG. 3(b), the second segments 26 are a plurality of separate coatings coated on the surface of the needle body 22, and areas of the needle body 22 that are not covered by the plurality of separate coatings form the plurality of first segments 24. It is noted that the order of arrangement of the first segment 24 and the second segment 26 are not limited to the illustrated embodiments in FIGS. 3(a) and 3(b). That is, what the insulating part 21 is directly connected to may be the first segment 24 or the second segment 26, and what the pinpoint 28 is directly connected to may be the first segment 24 or the second segment 26. In additional, the order of the arrangement of the first segments 24 and the second segments 26 will not affect the radiofrequency ablation effect of the radiofrequency ablation electrode needle 20.

Figure 3C:
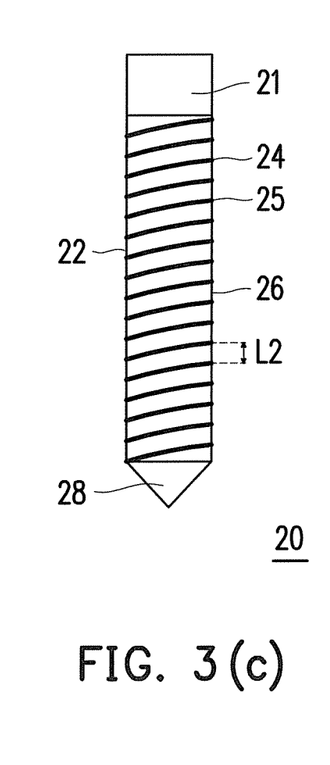
Figure 3D:
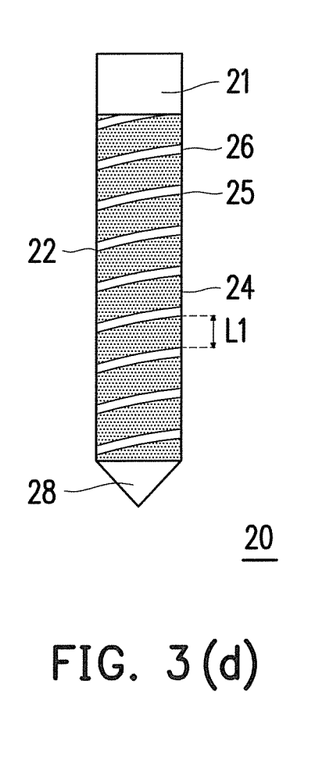

FIG. 3(c) is a schematic diagram of a radiofrequency ablation electrode needle according to the other exemplary embodiment of the disclosure. FIG. 3(d) is a schematic diagram of a radiofrequency ablation electrode needle according to still another exemplary embodiment of the disclosure. In the embodiment, the first segments 24 and the second segments 26 are exposed on the surface of the needle body 22 by using a spring 25 sleeved outside the needle body 22. In the embodiment of FIG. 3(c), the spring 25 sleeves outside the needle body 22 to form the first segments 24, and areas of the needle body 22 that are not covered by the spring 25 form the second segments 26. In the embodiment of FIG. 3(d), the spring 25 sleeves outside the needle body 22 to form the second segments 26, and areas of the needle body 22 that are not covered by the spring 25 form the first segments 24.

Figure 3E:
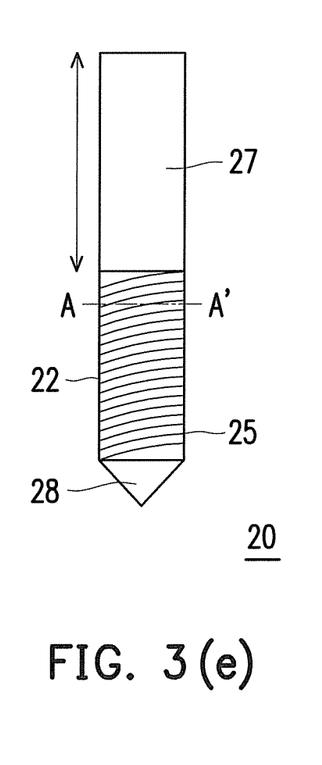

FIG. 3(e) is a schematic diagram of a radiofrequency ablation electrode needle according to an exemplary embodiment of the disclosure. In an embodiment as shown in FIG. 3(e), an end of the spring 25 is connected to a slider 27, and a length of the spring 25 sleeved outside the needle body 22 is adjustable by the slider 27, so as to change the ablation size of the radiofrequency ablation electrode needle 20.

In the embodiments of FIGS. 3(a)-3(e), the plurality of first segments 24 of the radiofrequency ablation electrode needle 20 have the same length and the range of a length L1 of the plurality of first segments 24 is between 0.1-1 mm. On the other hand the plurality of second segments 26 of the radiofrequency ablation electrode needle 20 may have the same length or different lengths, and the range of a length L2 of the plurality of second segments 26 is between 0.1-2 mm. More specifically, the length L1 of the plurality of first segments 24 and the length L2 of the plurality of second segments 26 need to be carefully designed to make efficient and even ablation possible. Since both the interlaced arrangement of the plurality of first segments 24 and the plurality of second segments 26 and the impedance difference between the plurality of first segments 24 and the plurality of second segments 26—may cause the spatial distribution of the electric field of the radiofrequency ablation electrode needle 20 discontinuous, the ablation will occur in an area around the plurality of first segments 24. If the length L1 of the plurality of first segments 24 is too large, the tissue surrounding the plurality of first segments 24 may necrotize too fast, which will cause the impedance to be higher than the initial impedance threshold in a very short period of time, and force the radiofrequency generator 10 to temporally stop operating in the operation mode of impedance control. If the length L2 of the plurality of second segments 26 is too large, the ablation areas corresponding to two immediately adjacent first segments 24 will be separated from each other and cause an uneven ablation.

In the embodiment of FIG. 3(c), the range of the length L2 of the plurality of second segments 26 is between 0.1-2 mm, so a pitch of the spring 25 has a range between 0.1-2 mm. The range of the length L1 of the plurality of first segments 24 is between 0.1-1 mm, so a line width W of the spring 25 has a range between 0.1-1 mm. In the embodiment of FIG. 3(d), the range of the length L2 of the plurality of second segments 26 is between 0.1-2 mm, so the line width W of the spring 25 has a range between 0.1-2 mm. The range of the length L1 of the plurality of first segments 24 is between 0.1-1 mm, so the pitch of the spring 25 has a range between 0.1-1 mm.

Figure 3F:
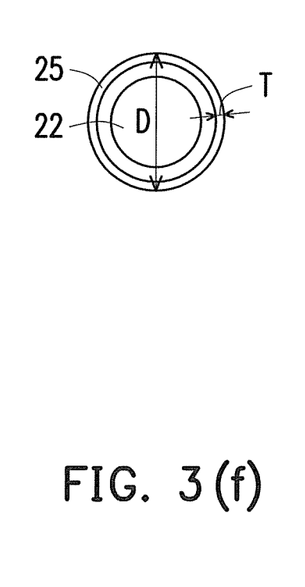
FIG. 3(f) is a cross-sectional view of a radiofrequency ablation electrode needle in the embodiment of FIG. 3(e) alone line A-A'.

FIG. 3(f) is a cross-sectional view of a radiofrequency ablation electrode needle in the embodiment of FIG. 3(e) along line A-A'. Because the spring 25 sleeves outside the surface of the needle body 22, a thickness T of the spring 25 will affect the diameter D of the radiofrequency ablation electrode needle 20. Take the most popular used size 12-19 G (Gauge) of the radiofrequency ablation electrode needle as an example, the thickness T of the spring 25 may have a range between 0.1-0.75 mm to prevent the whole diameter D of the radiofrequency ablation electrode needle 20 from being excessively large.

Figure 4:
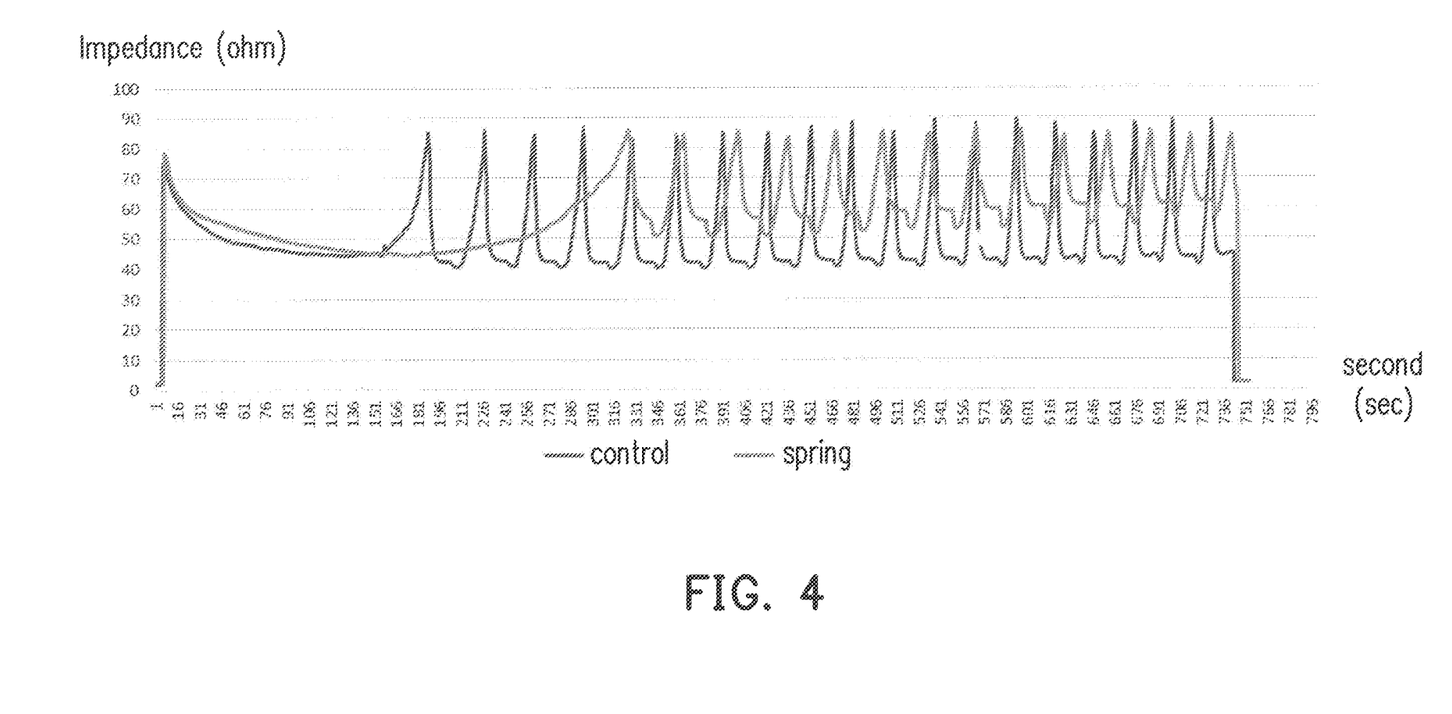
FIG. 4 is a graph showing an impedance v. ablation time relationship of the radiofrequency ablation electrode needle in the embodiment of FIG. 3(c) and the control electrode needle during a radiofrequency ablation therapy.

FIG. 4 shows an impedance v. ablation time relationship of control group and the radiofrequency ablation electrode needle 20 in the embodiment of FIG. 3(c) during a radiofrequency ablation therapy. In FIG. 4, the "control" curve represents the impedance v. ablation time relationship for the control group which is a radiofrequency ablation electrode needle with the second segment 26 continuously covered by the first segment 24, and the "spring" curve represent the impedance v. ablation time relationship for the radiofrequency ablation electrode needles 20 in the embodiment of FIG. 3(c). As shown in FIG. 4, it takes about 181 seconds for the control group of the electrode needle to cause the impedance to reach the initial impedance threshold. On the other hand, it takes much longer for the radiofrequency ablation electrode needle 20 to cause the impedance to reach the initial impedance threshold. In other words, the radiofrequency ablation electrode needle 20 can operate much longer before it is forced to temporarily stop when the impedance reaches the initial impedance threshold. In addition, a comparison of the radiofrequency ablation electrode needle 20 of FIG. 3(c) and the control group of the electrode needle is also made with respect to the ablation time and the ablation volume. More specifically, after 12 minutes of the radiofrequency ablation therapy to a liver tissue or after 12 kcal energy deposited to a local liver tissue, the control group of the electrode needle forms an ablation area with three (i.e., x, y, z) axial lengths of 3.6 cm, 3.0 cm, and 3.0 cm, respectively. On the other hand, the radiofrequency ablation electrode needle 20 of FIG. 3(c) only takes 3 minutes and 45 seconds to form an ablation area with three (i.e., x, y, z) axial lengths of 3.6 cm, 3.1 cm, and 3.0 cm respectively. In other words, the radiofrequency ablation electrode needle 20 of FIG. 3(c) is more efficient than the commercial stainless steel radiofrequency ablation electrode needle, because it only takes ⅓ treatment time of the control group of the electrode needle to achieve the same ablation area/volume.

In view of the embodiments shown in FIGS. 3(a)-3(f), by using the impedance difference between the first segments 24 and the second segments 26 and the arrangement of the equal length of the first segments 24, the spatial distribution of the electric field of the radiofrequency ablation electrode needle 20 is discontinuous and provides a slower necrotic rate of the tissue surrounding the radiofrequency ablation electrode needle 20. As a result, it takes much longer to cause the impedance to reach the initial impedance threshold due to the slower necrotic rate of the tissue. Besides, due to the less necrotic surrounding tissue, the heating energy can be distributed more effectively in conduction and convection manner, thereby significantly reducing the treatment time of the radiofrequency ablation therapy and achieving rapid ablation.

Figure 5A:
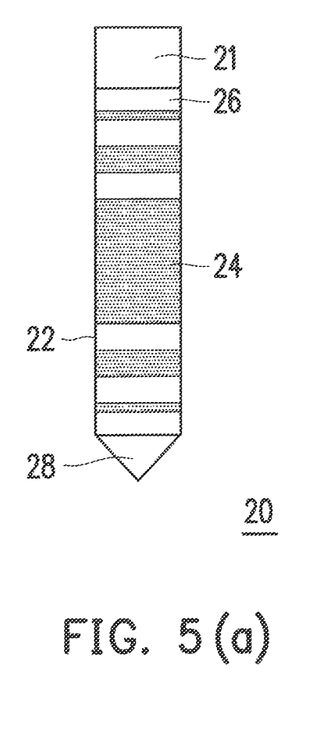
FIGS. 5(a)-5(c) are schematic diagrams of a radiofrequency ablation electrode needle according to exemplary embodiments of the disclosure.
Figure 5B:
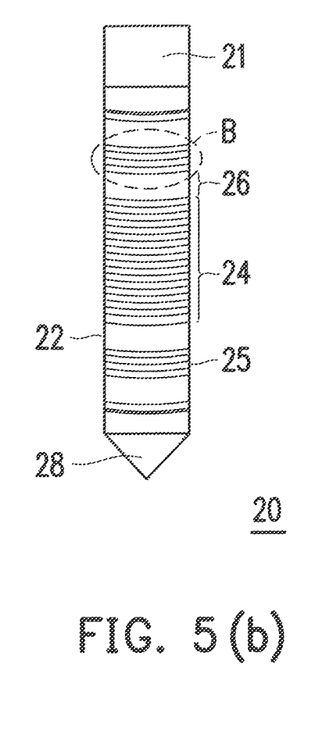
Figure 5C:
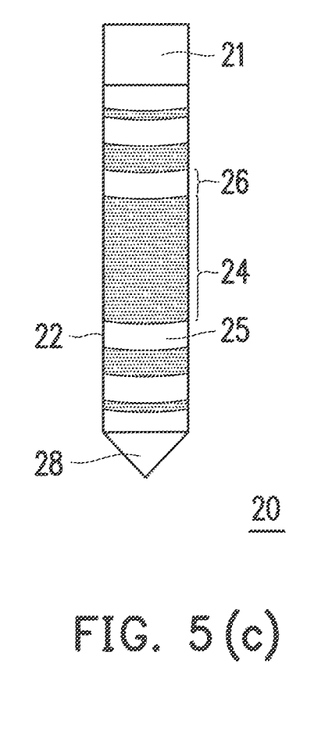

FIGS. 5(a)-5(c) are schematic diagrams of a radiofrequency ablation electrode needle according to exemplary embodiments of the disclosure. In the embodiments of FIG. 5(a), FIG. 5(b) and FIG. 5(c), the radiofrequency ablation electrode needle 20 comprises a plurality of first segments 24, and two immediately adjacent ones of the plurality of first segments 24 have different lengths. More specifically, the plurality of first segments 24 are symmetrically disposed to a center of the needle body 22. The closer the plurality of first segments 24 to either of two opposite ends of the needle body 22, the shorter the length of the plurality of first segments 24, and the closer the plurality of first segments 24 to the center of the needle body, the longer the length of the plurality of first segments 24. That is to say, the lengths of the plurality of first segments 24 closer to the insulating part 21 and the pinpoint 28 are shorter, and the lengths of the plurality of first segments 24 closer to the center of the needle body 22 are longer. It is noted that the arrangement of the plurality of first segments 24 and the plurality of second segment 26 should be carefully designed. In particular, one of the plurality of first segments 24 should be located at the center of the needle body 22, and the plurality of second segment 26 and the rest of the plurality of first segments 24 are then alternately disposed from the one of the plurality of first segments 24 located at the center of the needle body 22 toward both ends of the needle body 22. By using the above-noted arrangement of the plurality of first segments 24 and the plurality of second segment 26, the radiofrequency ablation electrode needle 20 will have a sphere-like ablation shape. In another embodiment, the insulating part 21 further directly connects to one of the plurality of second segment 26, and the pinpoint 28 further directly connects to the other one of the plurality of second segment 26, which may adjust the ablation shape further closer to a sphere.

In the embodiment of FIG. 5(a), the plurality of first segments 24 is exposed on the surface of the needle body 22 in a coated manner. However, in another embodiment, the plurality of second segment 26 may also be exposed on the surface of the needle body 22 in a coated manner. In the embodiments of FIG. 5(b) and FIG. 5(c), the plurality of first segments 24 and the plurality of second segment 26 are exposed on the surface of the needle body 22 with a spring 25 sleeving outside the needle body 22 respectively. In the embodiment of FIG. 5(b), the spring 25 sleeves outside the needle body 22 to form the plurality of first segments 24, and areas of the needle body 22 that are not covered by the spring 25 form the plurality of second segments 26. In the embodiment of FIG. 5(c), the spring 25 sleeves outside the needle body 22 to form the plurality of second segments 26, and areas of the needle body 22 that are not covered by the spring 25 form the plurality of first segments 24. It is noted that the spring 25 covers a partial surface of the needle body 22 by a unified line width W to form the plurality of first segments 24 or the plurality of second segments 26 such as FIG. 5(b). However, in another embodiment, the spring 25 covers a partial surface of the needle body 22 by difference line widths W to form the plurality of first segments 24 or the plurality of second segments 26 such as FIG. 5(c).

Besides, in some embodiments, each of the radiofrequency ablation electrode needle 20 in the embodiments of FIGS. 5(a)-5(c) further comprises an insulating cover 23 or a slider 27 similar to aforementioned embodiments.

Table 1 shows the radiofrequency ablation results of by the control group of the radiofrequency ablation electrode needle and the radiofrequency ablation electrode needle 20 in the embodiment of FIG. 5(b) with the same parameters. Table 2 shows the radiofrequency ablation results by the control group of the radiofrequency ablation electrode needle and the radiofrequency ablation electrode needle 20 in the embodiment of FIG. 5(c) with the same parameters.

The lengths of the control group of the radiofrequency ablation electrode needle and the radiofrequency ablation electrode needle 20 are 3 cm. The exposed length of the control group of the radiofrequency ablation electrode needle is adjusted by an insulating cover 23, and the exposed length of the radiofrequency ablation electrode needle 20 is adjusted by the slider 27. In Table 1 and Table 2, z/x and y/x represent the ratio of the lengths measured in different directions x, y, z respectively.

TABLE 1

| | | Exposed length | | |
|---|---|---|---|---|
| | | 3 cm | 2 cm | 1 cm |
| control group of the radiofrequency ablation electrode needle | z/x | 3.2/4.0 = 0.80 | 2.6/3.0 = 0.87 | 1.8/1.4 = 1.28 |
| | y/x | 3.2/4.0 = 0.80 | 2.7/3.0 = 0.90 | 1.8/1.4 = 1.28 |
| | volume | 21.43 cm3 | 11.02 cm3 | 2.37 cm$^3$ |
| radiofrequency ablation electrode needle in FIG. 5(b) | z/x | 3.0/3.5 = 0.86 | 3.0/3.0 = 1.00 | 1.7/1.6 = 1.06 |
| | y/x | 3.0/3.5 = 0.86 | 3.2/3.0 = 1.07 | 1.8/1.6 = 1.12 |
| | volume | 16.48 cm3 | 15.07 cm3 | 2.56 cm$^3$ |

TABLE 2

| | | Exposed length | | |
|---|---|---|---|---|
| | | 3 cm | 2 cm | 1 cm |
| control group of the radiofrequency ablation electrode needle | z/x | 2.8/3.5 = 0.80 | 2.4/2.5 = 0.96 | 1.4/1.5 = 0.9 |
| | y/x | 2.6/3.5 = 0.74 | 2.2/2.5 = 0.88 | 1.5/1.5 = 0.93 |
| | volume | 13.33 cm$^3$ | 6.90 cm$^3$ | 1.64 cm$^3$ |
| radiofrequency ablation electrode needle in FIG. 5(c) | z/x | 3.0/3.6 = 0.83 | 2.5/2.5 = 1.00 | 1.5/1.5 = 1.00 |
| | y/x | 3.0/3.6 = 0.83 | 2.4/2.5 = 0.96 | 1.5/1.5 = 1.00 |
| | volume | 16.95 cm$^3$ | 7.85 cm$^3$ | 1.76 cm$^3$ |

As shown in Table 1 and Table 2, the radiofrequency ablation electrode needle 20 has similar ratios z/x and y/x, which clearly shows that the radiofrequency ablation electrode needle 20 can generate a sphere-like ablation shape.

Figure 6:
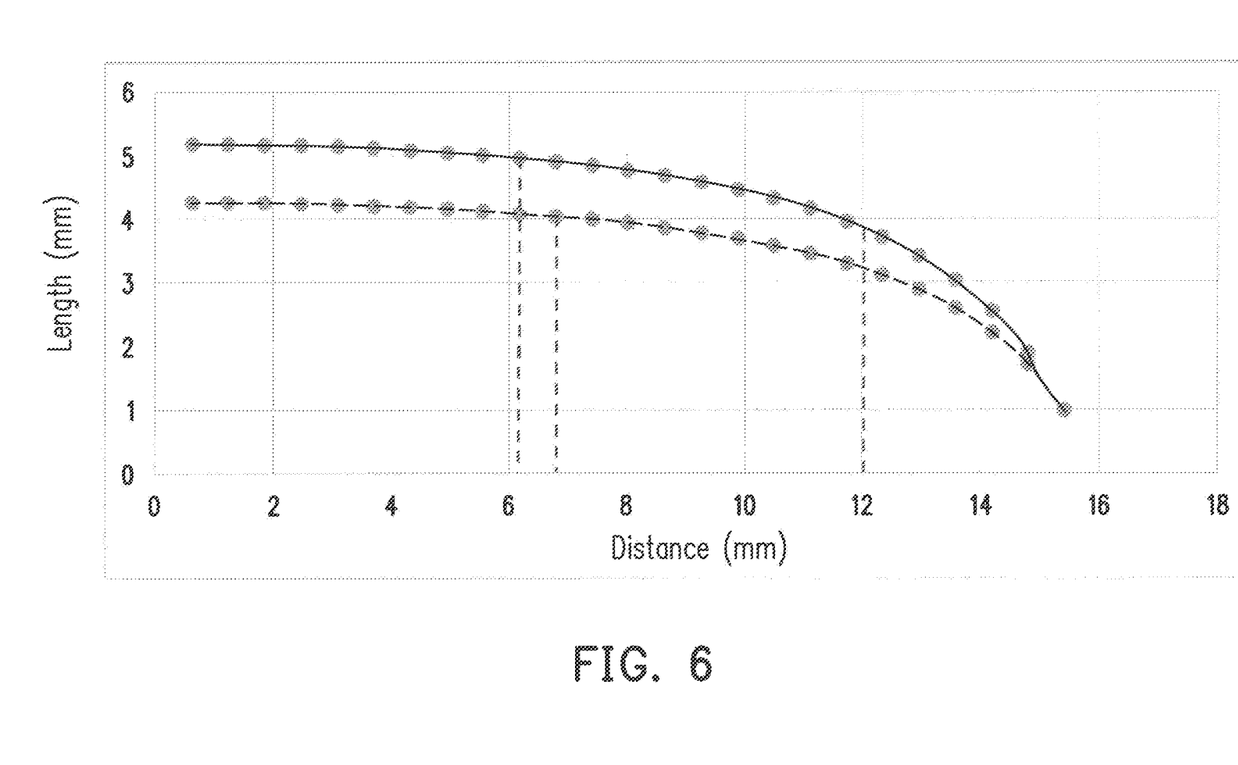
FIG. 6 shows the relationship between a position and a length of the first segment when the radiofrequency ablation electrode needle of the embodiment of the disclosure has a sphere-like ablation shape in accordance with an embodiment of the disclosure.

FIG. 6 is a graph showing the relationship between a position and a length of the first segment 24 when the radiofrequency ablation electrode needle 20 of the embodiment of the disclosure has a sphere-like ablation shape in accordance with an embodiment of the disclosure. In FIG. 6, the X axis represents a distance of the first segment 24 from the center of the needle body 22 in an X direction parallel to the axis of the radiofrequency ablation electrode needle 20. The Y axis represents a length of the first segment 24 in the X direction when the radiofrequency ablation electrode needle 20 has a sphere-like ablation shape. The "solid line" curve represents the data after reducing a radius (0.72 mm) of the radiofrequency ablation electrode needle 20. The "dotted line" curve represents the data neglected the radius of the radiofrequency ablation electrode needle 20. In the embodiment, the length of the needle body 22 is 30 mm, the plurality of first segments 24 are five first segments 24, two immediately adjacent ones of the plurality of first segments 24 are separated from one of the second segments 26 with a length of 2 mm, and two of the plurality of first segments 24 connect to the insulating part 21 and the pinpoint 28 respectively. The length of the first segments 24 at an opposite distal end of the needle body 22 is 1 mm, and the length of the first segments 24 at a position of 12 mm away from the center of the needle body 22 has a range between 3.1-3.9 mm. Since one first segment 24 will be located at the center of the needle body 22 needs to be maintained as the first segment 24, after reducing a length of pinpoint 28 (4 mm), the length of the first segment 24 at the center of the needle body 22 has a range between 8.2-9.8 mm. Considering the process/manufacturing error, a length ratio of the five first segments 24 in an order from one distal end such as the insulating part 21 of the needle body 22 toward the opposite distal end such as the pinpoint 28 of the needle body 22 is 1:a:b:c:1, wherein a and c have a range between 3-4, and b has a range between 8-10.

Figure 5D:
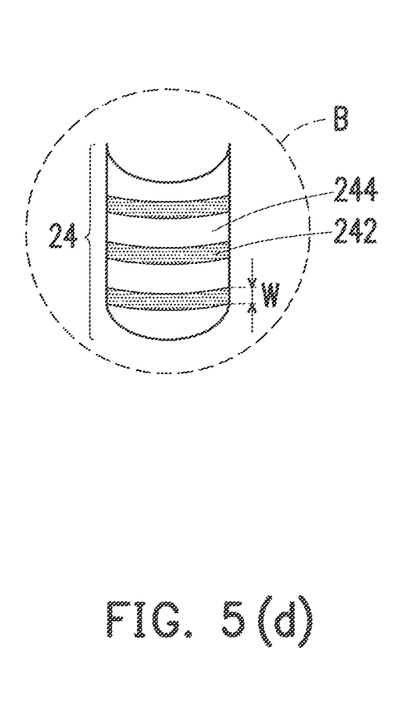
FIG. 5(d) is a partial enlarged view of area B of the radiofrequency ablation electrode needle in the embodiment of FIG. 5(b)

FIG. 5(d) is a partial enlarged view of area B of the radiofrequency ablation electrode needle in the embodiment of FIG. 5(b). In the illustrated embodiment, the spring 25 has a smaller line width W, so each one of the first segments 24 further comprises at least one first sub-segment 242 and at least two second sub-segments 244. An impedance of the at least one first sub-segment 242 is smaller than an impedance of the at least two second sub-segments 244, and at least one of the at least one first sub-segment 242 is disposed between two immediately adjacent of the at least two second sub-segments 244. Besides, in another embodiment, there are a plurality of first sub-segments 242, and the plurality of first sub-segments have a same length. By using the impedance difference between the first sub-segments 242 and the second sub-segments 244 and the arrangement of the equal length of the first sub-segments 242, the spatial distribution of the electric field of the radiofrequency ablation electrode needle 20 is discontinuous. Thus, the radiofrequency ablation electrode needle 20 can provide rapid ablation with a sphere-like ablation shape.

Figure 7:
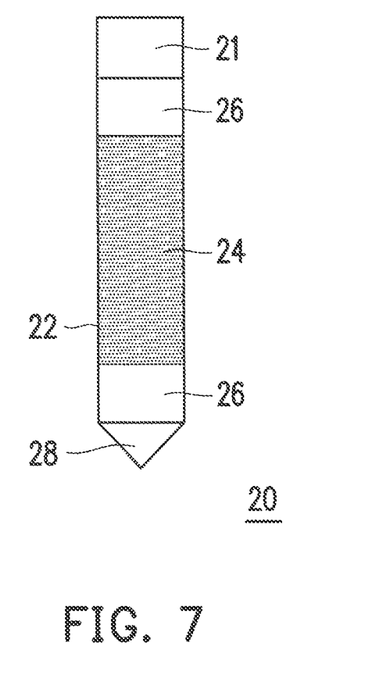
FIG. 7 is a schematic diagram of a radiofrequency ablation electrode needle according to an exemplary embodiment of the disclosure.

FIG. 7 is a schematic diagram of a radiofrequency ablation electrode needle according to an exemplary embodiment of the disclosure. In FIG. 7, the needle body 22 comprises a first segment 24 and two second segments 26. The first segment 24 is disposed at the central portion of the needle body 22, and the two second segments 26 are disposed at two opposite ends of the needle body 22 respectively. In an embodiment, the difference between the impedance of the first segment 24 and the second segments 26 is the same with the embodiments that mentioned above, it is not repeated thereto.

In the embodiment of FIG. 7, the first segment 24 is a coating coated on the surface of the needle body 22, and areas of the needle body 22 that are not covered by the coating form the second segments 26. However, in another embodiment, the second segments 26 are two separate coatings coated on the surface of the needle body 22, and areas of the needle body 22 that are not covered by the coatings form the first segment 24.

In the embodiment of FIG. 7, the insulating part 21 further directly connects to one of the second segments 26, the pinpoint 28 further directly connects to the other second segment 26, and the first segment 24 should be located at the center of the needle body 22. By using the above-noted arrangement of the first segment 24 and the two second segments 26, the radiofrequency ablation electrode needle 20 will have a sphere-like ablation shape.

As aforementioned, the radiofrequency ablation electrode needle of the disclosure can provide rapid ablation and/or sphere-like ablation shape by using the impedance difference between the first segment and the second segments and the arrangement of the first segment and the second segments accompanied with the changes of the length of the first segment.

It will be apparent to those skilled in the art that various modifications and variations can be made to the disclosed embodiments. It is intended that the specification and examples be considered as exemplars only, with a true scape of the disclosure being indicated by the following claims and their equivalents.

What is claimed is:

1. A radiofrequency ablation electrode needle, comprising:
 a needle body comprising at least one first segment and at least two second segments, wherein the at least one first segment and the at least two second segments are exposed on a surface of the needle body, wherein an impedance of the at least one first segment is smaller than an impedance of the at least two second segments, at least one of the at least one first segment is disposed between two immediately adjacent ones of the at least two second segments, and the radiofrequency ablation electrode needle is a monopolar electrode needle,
 wherein the at least one first segment includes a plurality of first segments, and the plurality of first segments are electrically connected,
 wherein two immediately adjacent ones of the plurality of first segments have different lengths.

2. The radiofrequency ablation electrode needle as claimed in claim 1, wherein a difference between the impedance of the at least one first segment and the impedance of the at least two second segments is at least $10^6 \Omega$.

3. The radiofrequency ablation electrode needle as claimed in claim 1, further comprising an insulating cover disposed outside the needle body, wherein the insulating cover is extendable and retractable to selectively expose some of the at least one first segment and the at least two second segments.

4. The radiofrequency ablation electrode needle as claimed in claim 1, wherein a pinpoint of the needle body is electrically insulated.

5. The radiofrequency ablation electrode needle as claimed in claim 1, wherein the plurality of first segments are a plurality of separate coatings coated on the surface of the needle body, and areas of the needle body that are not covered by the plurality of separate coatings form the at least two second segments.

6. The radiofrequency ablation electrode needle as claimed in claim 1, wherein the at least two second segments are a plurality of separate coatings coated on the surface of the needle body, and areas of the needle body that are not covered by the plurality of separate coatings form the plurality of first segments.

7. The radiofrequency ablation electrode needle as claimed in claim 1, wherein a spring sleeved outside the needle body forms the plurality of first segments, and areas of the needle body that are not covered by the spring form the at least two second segments.

8. The radiofrequency ablation electrode needle as claimed in claim 7, wherein an end of the spring is connected to a slider, and a length of the spring sleeved outside the needle body is adjustable by the slider.

9. The radiofrequency ablation electrode needle as claimed in claim 1, wherein a spring sleeved outside the needle body forms the at least two second segments, and areas of the needle body that are not covered by the spring form the plurality of first segments.

10. The radiofrequency ablation electrode needle as claimed in claim 9, wherein an end of the spring is connected to a slider, and a length of the spring sleeved outside the needle body is adjustable by the slider.

11. The radiofrequency ablation electrode needle as claimed in claim 1, wherein the closer the plurality of first segments to either of two opposite ends of the needle body, the shorter the length of the plurality of first segments, and the closer the plurality of first segments to a center of the needle body, the longer the length of the plurality of first segments.

12. The radiofrequency ablation electrode needle as claimed in claim 1, wherein the plurality of first segments are symmetrically disposed to a center of the needle body.

13. The radiofrequency ablation electrode needle as claimed in claim 1, wherein the plurality of first segments are five first segments, a length ratio of the five first segments in an order from one distal end of the needle body toward an opposite distal end of the needle body is 1:a:b:c:1, wherein a and c have a range between 3-4, and b has a range between 8-10.

14. The radiofrequency ablation electrode needle as claimed in claim 1, wherein each first segment further comprises at least one first sub-segment and at least two second sub-segments, wherein a impedance of the at least one first sub-segment is smaller than a impedance of the at least two second sub-segments, and at least one of the at least one first sub-segment is disposed between two immediately adjacent of the at least two second sub-segments.

15. The radiofrequency ablation electrode needle as claimed in claim 14, wherein the at least one first sub-segment includes a plurality of first sub-segments, and the plurality of first sub-segments have a same length.

16. The radiofrequency ablation electrode needle as claimed in claim 1, wherein the at least one first segment is disposed at a center of the needle body, and two of the at least two second segments are disposed at two opposite ends of the needle body.

17. The radiofrequency ablation electrode needle as claimed in claim 16, wherein the at least one first segment is a coating coated on the surface of the needle body, and areas of the needle body that are not covered by the coating form the at least two second segments.

18. The radiofrequency ablation electrode needle as claimed in claim 16, wherein the at least two second segments are a plurality of separate coatings coated on the surface of the needle body, and an area of the needle body that are not covered by the plurality of separate coatings form the at least one first segment.

19. A radiofrequency ablation electrode needle, comprising:
a needle body comprising at least one first segment and at least two second segments, wherein the at least one first segment and the at least two second segments are exposed on a surface of the needle body, wherein an impedance of the at least one first segment is smaller than an impedance of the at least two second segments, at least one of the at least one first segment is disposed between two immediately adjacent ones of the at least two second segments, and the radiofrequency ablation electrode needle is a monopolar electrode needle,
wherein the at least one first segment includes a plurality of first segments, and the plurality of first segments are electrically connected,
wherein the plurality of first segments have a same length.

* * * * *